United States Patent
Cavanagh et al.

[11] Patent Number: 5,693,058
[45] Date of Patent: Dec. 2, 1997

[54] OBSTETRIC VACUUM EXTRACTOR

[76] Inventors: Alexander J. M. Cavanagh, Gludy, Brecon, Powys LD3 9PE; Carlton C. Hobbs, 8 Ridge Road, Kingswinford, West Midlands DY6 9RD, both of Great Britain

[21] Appl. No.: 660,256

[22] Filed: Jun. 7, 1996

[30] Foreign Application Priority Data

Jun. 9, 1995 [GB] United Kingdom ............... 9511795

[51] Int. Cl.⁶ ............................................. A61B 17/42
[52] U.S. Cl. ............................................. 606/123; 606/119
[58] Field of Search ................... 606/1, 119–123; 600/201, 204, 207

[56] References Cited

U.S. PATENT DOCUMENTS 3,765,408  10/1973  Kawai ............................... 606/123
5,019,086  5/1991  Neward ............................ 606/123
5,224,947  7/1993  Cooper et al. .................... 606/123

FOREIGN PATENT DOCUMENTS 31358589  4/1983  Germany ........................ 606/123
3535055   2/1987  Germany ........................ 606/123
0839518   6/1981  U.S.S.R. .......................... 606/123

Primary Examiner—Glenn K. Dawson
Attorney, Agent, or Firm—Caesar, Rivise, Bernstein, Cohen & Pokotilow, Ltd.

[57] ABSTRACT

An obstetric vacuum extractor is provided for assistance in the delivery of a baby. The extractor includes a suction cup of flexible polymeric material to be attached to a portion of the head of a baby. The cup has a flexible integrally formed hollow extension for connection to a source of vacuum and also being connectable to a handle. The cup also has an internal integral skirt extending from its inner surface, the skirt extending adjacent to the rim of the cup.

19 Claims, 3 Drawing Sheets

OBSTETRIC VACUUM EXTRACTOR

This invention relates to an obstetric vacuum extractor used to provide assistance in the delivery of a baby.

When a baby is delivered vaginally, assistance is required in about 10% of cases. The assistance has traditionally been provided by medical forceps but more recently vacuum extractors have been proposed and used. Initially the vacuum extractors were made of metal but a suction rubber type, known as a SILASTIC cup has also been used.

The known vacuum extractors compose a cup to be attached to the head of the baby to be delivered and a hollow shaft through which a vacuum can be applied to the cup. Although advantageous in specific circumstances, both the above-mentioned known types of extractor are relatively expensive. At present metal cups of different patterns are required for various positions of the baby's head and SILASTIC cups are of such a shape and size that they can normally only be satisfactorily used when the baby's head is in the occiput-anterior position.

The invention aims to provide an improved vacuum extractor that can be used to produce traction in any required direction while minimising the danger of damage to the baby's scalp.

Accordingly, the invention provides a vacuum extractor comprising a suction cup of flexible polymeric material to be attached to a portion of the head of a baby, the cup having a flexible integrally-formed external hollow extension for connection to a source of vacuum and also being connectable to a handle, and the cup having an internal integral skirt extending from its inner surface, the skirt extending adjacent to the rim of the cup.

Preferably the skirt extends parallel to the rim of the cup.

Preferably the cup is of generally frusto-spherical shape. It is preferably less than a full hemisphere in shape and is thus dome-shaped, having a polar region away from its substantially circular rim.

In the preferred embodiment, therefore, the skirt is also of circular plan form and it extends continuously around the inner surface of the cup.

The internal skirt enables good sealing contact to be made and maintained with a bay's head and the position of the seal inside the cup is protected during application to the head and during use by the outer rim of the cup, which can act as a protective shield. Thus the risk of a portion of the sealing circumference of the skirt being folded inwardly during application of the cup to a head is greatly reduced or eliminated so that a good sealing contact for the applied vacuum can be consistently achieved. Without this 'dual lip' feature, i.e. the internal skirt protected by the outer rim, there is a serious risk of a portion of the rim of the cup, particularly due to its necessarily flexible nature, being folded inwardly during application to a baby's head. The 'dual lip' feature is particularly beneficial in view of the non-uniform nature of a baby's head in that sealing may be effected in certain instances by the outer rim, in other instances by the inner skirt and, possibly, by a combination of the two.

The inside frusto-spherical surface of the cup preferably has a series of channels spreading from a central, i.e. polar, vacuum entry port, the latter leading directly into the hollow extension. By this means the vacuum effect can be spread around the interior surface of the cup, i.e. the surface which is to contact the baby's head.

The extension is preferably rotatable in use both in a plane parallel to the notional equatorial plane substantially of the cup and in a plane at right angles to that plane.

The hollow extension may be a short extension, e.g. 2–3 cms. long, into which is connected a longer hollow extension shaft, also of flexible polymeric material, or the integral extension may include the shaft and so extend for the full desired length, e.g. 12 to 20 cms. Although flexible, the extension and the shaft should be able to withstand a load of say, 10 kg without any substantial extension of their length.

The rotation may be achieved by the flexibility of the extension, its means of attachment to its shaft where used or a combination of both.

The cup may have a diameter of, for example, from 6 to 8 cms and a depth from its internal pole of 2 to 3 cms.

The internal skirt may have a radial length for example, of from about 1 to 4 mm and its free rim may be spaced from about 2 to 5 mm inside the outer rim of the cup.

The cup may be made by any convenient means, e.g. compression moulding of solid rubber or injection moulding of liquid rubber or flexible plastics material. For example, it may be made of a silicone rubber or a flexible polyurethane. It may have a wall thickness of e.g. 2 to 3 mm at the periphery and up to for example 10 mm at the pole. The circumference of the cup may be provided with a thickened rim, e.g. of 'O' ring section to reduce the risk of the rim folding inwardly during use. Moreover, because of the relatively thin wall of the cup between the outer rim and the inner skirt, the 'dual lips' can both readily flatten to conform the shape of the head to provide an excellent contact and seal.

The handle is preferably mounted transversely on the extension adjacent its end away from the cup. It may be a relatively rigid moulding of polymeric material, e.g. a polymeric layer moulded over a steel tube and be provided with suitably shaped finger holds. Thus the handle may be formed of a hollow steel tube having a centrally disposed transverse passageway to align with the longitudinal passageway through the shaft of the extractor. For example, a silicone rubber coating can be moulded over the steel tube so that it seals the longitudinal ends of the steel tube while leaving the transverse passageway open. A connector to join the handle to the extractor shaft can then be tightly forced through the transverse hole to give a vacuum-tight fit.

The extractors of the invention are relatively inexpensive to make and may be used as disposable items, i.e. the cup with extension and with handle, if desired may be disposed of after a single use.

The required vacuum may be applied from any convenient source, e.g. a central vacuum line or an electric or a hand pump. Vacuum of up to 24 to 26 inches of mercury may be needed and a gauge or other means is desirably employed to measure the vacuum applied.

In a preferred embodiment the vacuum extractor is provided with means to indicate that a force approaching the maximum that can safely be used is being approached. In a preferred embodiment the vacuum extractor is provided with means to ensure separation of the handle from the cup if a predetermined force is exceeded. The predetermined force may be, for example, 10 kg.

For example, the handle may gradually pull out of the extension or shaft as the force used increases and this may be indicated by the exposure of a coloured or other indicator on the extension or shaft. When a predetermined force is reached, the handle may be designed to pull entirely free.

Specific embodiments of the invention will now be described, by way of example only, with reference to the accompanying drawings in which.

Figure 1:
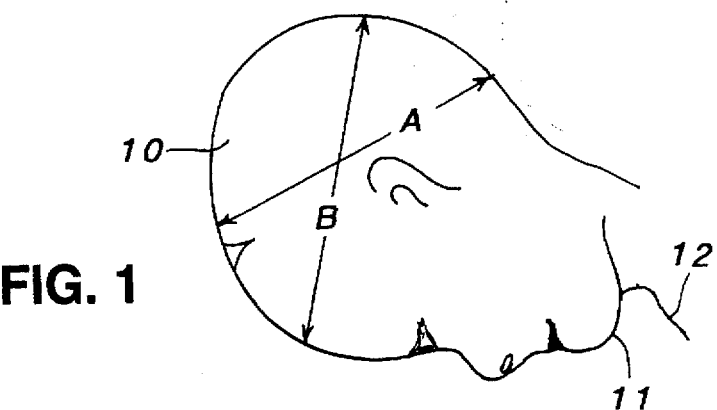
FIG. 1 is a diagrammatic representation of the head of a baby.

From FIG. 1, it can be seen that the effective diameter of the baby's head 10, diameter A, is smallest when the chin 11 is down towards the chest region 12, i.e. the occiput position. As the chin comes up away from the chest, the effective diameter of the head increases until diameter B is presented. Diameter B is too large for delivery.

Figure 2:
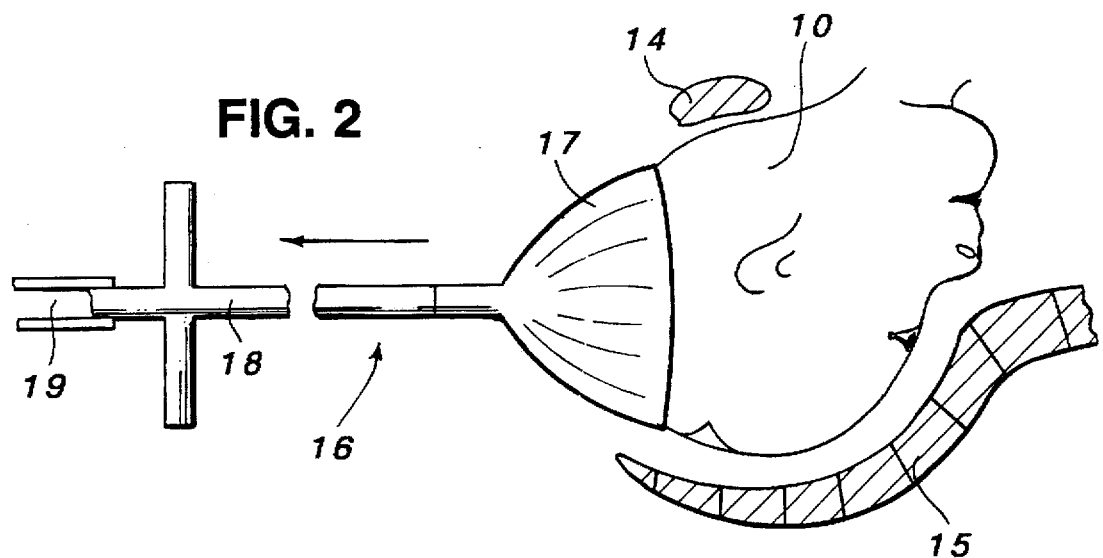
FIG. 2 is a diagrammatic representation showing the delivery of a baby using a prior vacuum extractor.
Figure 3:
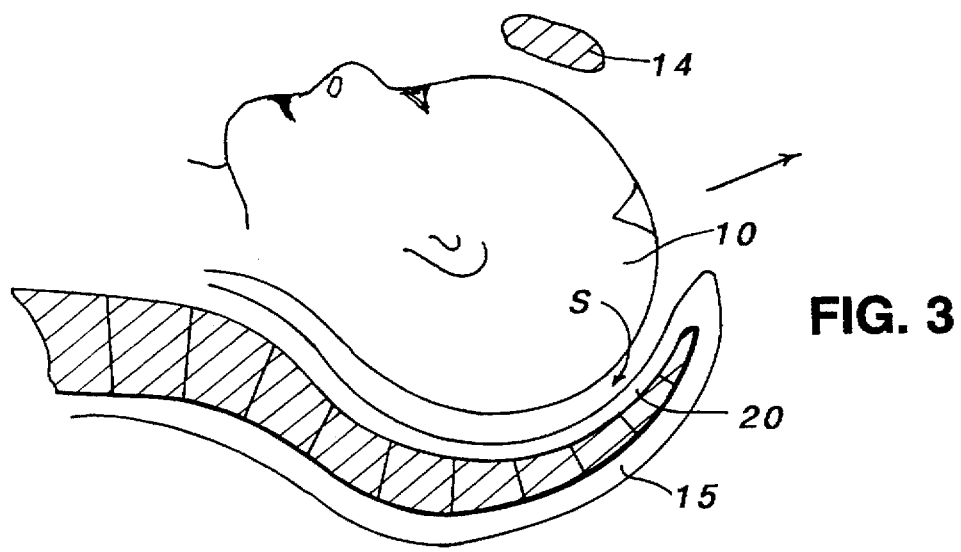
FIG. 3 is a diagrammatic representation showing the head of a baby in a difficult delivery position.

FIG. 2 shows a baby's head 10 between the pubis 14 and sacrum 15 in the occiputanterior position in which a relatively small diameter of head is presented for delivery and a prior art extractor 16, having a cup 17, connected via extension 18 to vacuum line 19, may be used. When the baby's head 10 is lying in the occiput-posterior position—see FIG. 3—, the problem is to insert a vacuum extractor into space S between the posterior vaginal wall 20 and head 10. The extractor 16 shown in FIG. 2 cannot easily be used in these circumstances. Extractors of the present invention, as described below, can be used in such circumstances.

In FIGS. 4 to 7 is shown a vacuum extractor 30 according to one embodiment of the invention. The device has a dome-shaped cup 31 of frusto-spherical shape to be attached to the head 10 of a baby. An extension 32 is integrally moulded in one piece with cup 31. Extension 32 is in the form of a hollow shaft that communicates to the interior of cup 31 at its pole. As shown, the shaft is moulded to extend generally tangentially to the cup to which it is joined by a curved end portion 32A. At its other end, extension shaft 32 fits into a transverse handle 33 having suitable moulded finger holds 34. Vacuum can be applied from a source (not shown) in the direction of A.

Depressions 35 and 36 have been moulded into the exterior surface of cup 31 to provide finger holds to assist in positioning the cup. A blister 37 is also moulded on to the exterior surface of the cup to provide orientation guide means.

Figure 4:
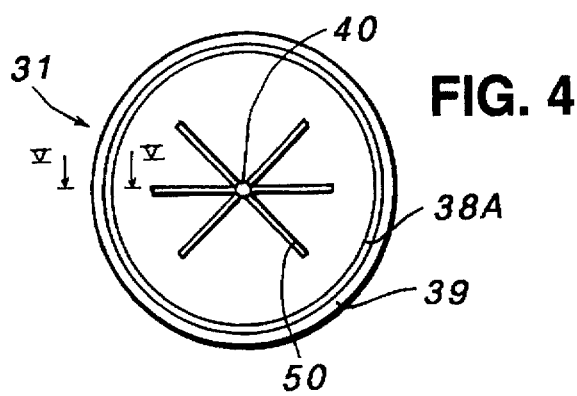
FIG. 4 is a plan view of the interior of the cup of one embodiment of the present invention.
Figure 5:
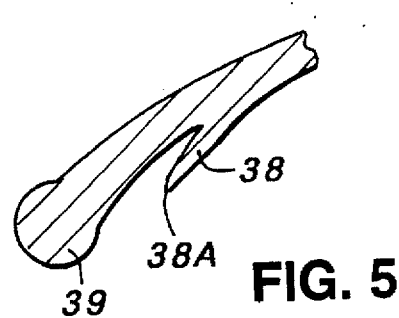
FIG. 5 is a section on the line V—V of FIG. 4.
Figure 6:
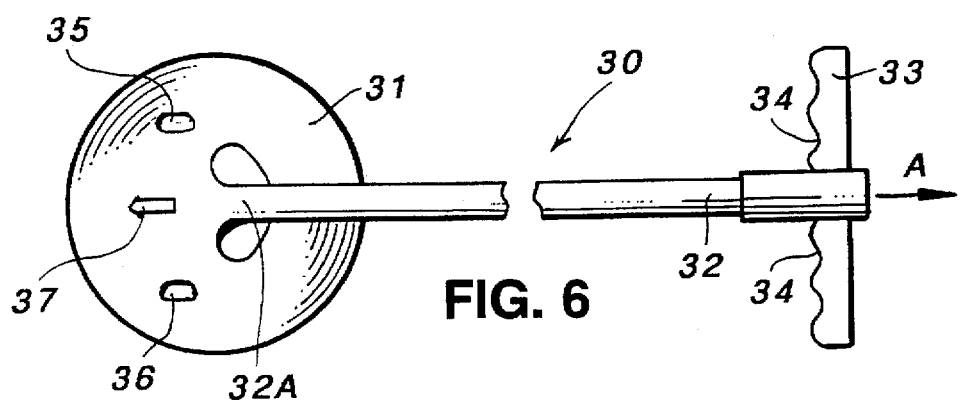
FIG. 6 is a plan view of the embodiment of FIG. 4 taken from the opposite side.
Figure 7:
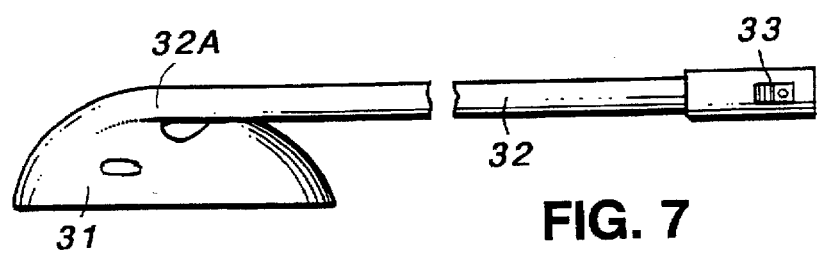
FIG. 7 is a side view of the embodiment of FIG. 6.

The extension shaft and the cup are moulded of flexible polymeric material so that the extension shaft can flex through at least 180° (preferably up to 360°) in a plane parallel to the equatorial plane of the cup and at least 180° in a plane perpendicular to the equatorial plane while still enabling the vacuum to be applied As shown in FIGS. 4 and 5, the cup has an integrally-moulded internal skirt 38 extending around to define an inner circumference 38A spaced from the outer circumference of the cup which is defined by a thickened rim or lip 39. At its internal pole 40 the cup has a hole communicating with a passageway through shaft 32 to the source of vacuum.

The inside surface of cup 31 is provided with channels 50 extending from the pole 40 towards the rim 39. Rim 39 is of increased thickness to reduce the risk of the cup folding inwardly when it is being attached to the baby's head. Channels 50 enable the applied vacuum effect to be more uniformly spread across the interior of the cup.

Figure 8:
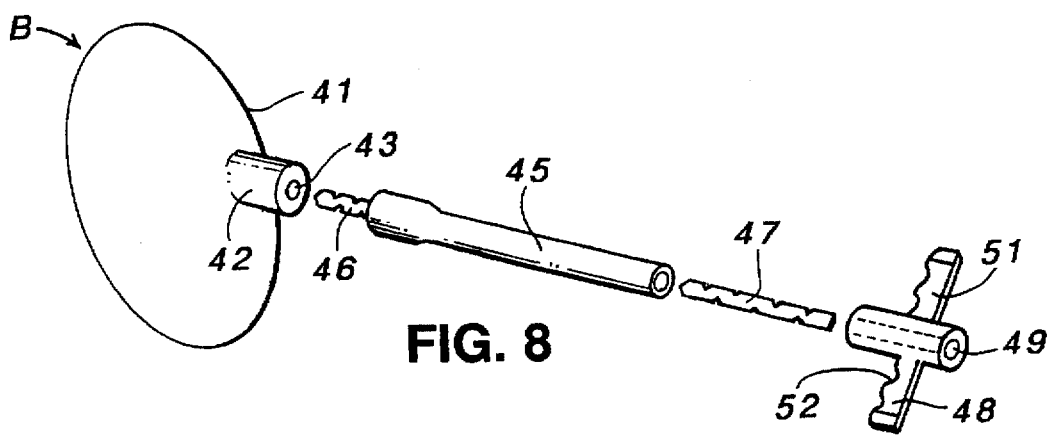
FIG. 8 is a perspective exploded view of a second embodiment of the present invention.

FIG. 8 illustrates another embodiment of the invention. In this second embodiment, cup 41 has a short, integral angled hollow extension 42 having a passageway 43 emerging at a hole 44 at its pole (FIG. 9) in a similar manner to the first embodiment. The extension is angled radially to the surface of the cup. A hollow extension shaft 45 is coupled to the free end of extension 42 via a polymeric or metal internal connector 46 which is forced partly into the hollow longitudinal passageway (not shown) in shaft 45 and partly into passageway 43 of extension 42. At its other end shaft 45 is connected via a similar polymeric or metal connector 47 to a handle 48. Handle 48 is similar to that shown in FIG. 6. It has a longitudinal passageway 49 for connection to a source of vacuum and a transverse handgrip 51 with moulded finger holds 52

The view along arrow B of FIG. 8 is similar to that of FIG. 4.

Figure 9:
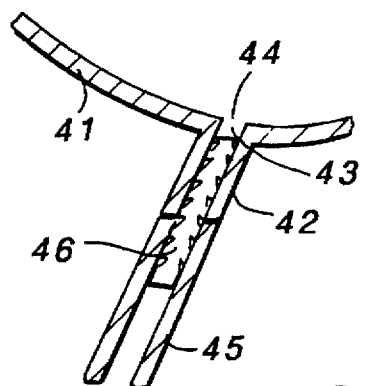
FIG. 9 is a sectional view of the unexploded embodiment of FIG. 8.

FIG. 9 illustrates the means of joining the shaft 45 to extension 42 using the connector 46. As shown, connector 46 is of length to extend part way along the hollow passageway 43 but not to reach and protrude at the pole 44 so that it cannot contact the baby's head.

Figure 10:
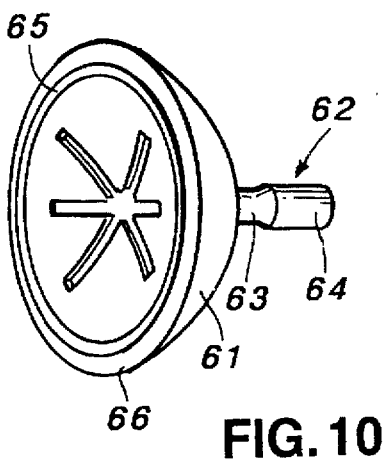
FIG. 10 is a perspective view of a third embodiment of the invention.

A third embodiment of the invention is shown in FIG. 10. Here cup 61 is integrally moulded with a short extension 62, which extension is normal to the exterior surface of the cup. Extension 62 has a narrow connecting neck portion 63 adjacent the cup and a wider portion 64. The narrow neck portion increases the flexibility of the extension relative to the cup and ensures that the connector used to join the extension to the shaft cannot reach the pole. Integral internal skirt 65 extends circumferentially inside outer rim 66.

Figure 11:
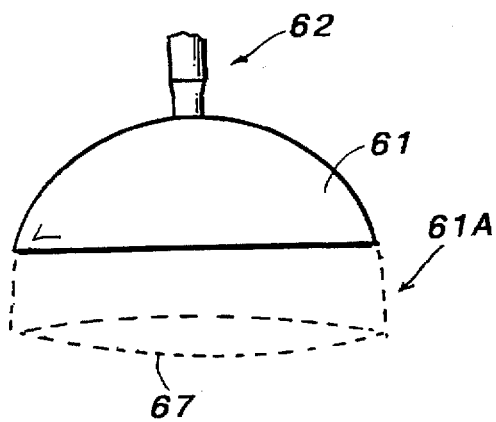
FIG. 11 is a diagrammatic illustration of the frusto-conical shape of the cup of the embodiment of FIG. 8.

As shown in FIG. 11, cup 61 is of frusto-hemispherical shape, the full hemi-sphere 61A being shown in dotted outline. Equator 67 defines the aforementioned notional equatorial plane of the cup.

Figure 12:
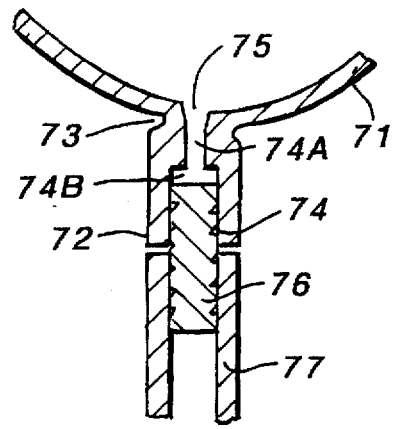
FIG. 12 is a sectional view of the extension region of a fourth embodiment.

In FIG. 12 is shown another embodiment in which cup 71 is also integrally moulded with a short extension 72. Extension 72 is narrowed somewhat immediately where it joins the surface of cup 71, thereby providing a groove 73 around the base of the extension. Groove 73 enables 180° rotation of the extension around its longitudinal axis without risk of collapsing and sealing of the tubular extensions.

If desired, the passageway 74 may be profiled to interlock with a corresponding profile on the connector.

The hollow passageway 74 inside extension 72 has a narrow portion 74A emerging at the polar hole 75 inside the cup and a wider portion 74B remote from the cup. Portion 74B is wide enough to accommodate a connector 76 whereby it can be joined to extension shaft 77 but connector 76 is too large to extend into portion 74A.

Figure 13:
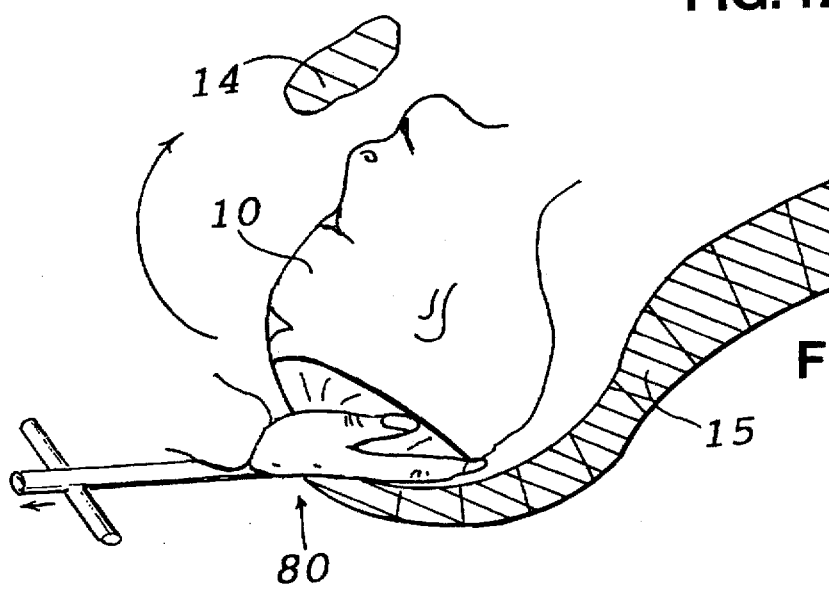
FIG. 13 is a diagrammatic illustration showing a device of the invention being positioned on a baby's head.

The embodiments of the invention described above enable a considerable degree of rotation of extractor shaft/extension to be obtained in use. Thus, the shaft and hence the handle may be rotated through 360° in the plane normal to the length of the extension/shaft and through 180° in the longitudinal plane of the shaft. The extractor can, therefore, be used to guide and provide traction so as to deliver a baby from almost any position from which vaginal delivery is clinically possible. FIG. 13 shows an extractor 80 of the invention being placed in position on a baby's head despite the head being in a similar occiput-posterior position to that shown in FIG. 3 and for which known extractors could not be used.

In all the variants of the invention the provision of the inner skirt within the outer rim of the cup enables an excellent vacuum seal to be obtained without serious risk of the skirt being folded inwardly during application of the cup to a baby's head and thereby endangering the baby's scalp and the effectiveness of the vacuum seal.

We claim:

1. An obstetric vacuum extractor comprising a suction cup of flexible polymeric material to be attached to a portion of the head of a baby, the cup having a rim, an inner surface, an exterior surface and a flexible integrally formed hollow extension adapted to be connected to a source of vacuum and a handle, and the cup having an internal integral skirt extending from the inner surface of the cup, the skirt having a rim extending adjacent to the rim of the cup, said skirt being able to form a seal in contact with the baby's head when vacuum is applied from said source of vacuum.

2. An obstetric vacuum extractor according to claim 1, in which the rim of the skirt extends parallel to the rim of the cup.

3. An obstetric vacuum extractor according to claim 1, in which the cup is of frusto-spherical shape having a substantially circular rim.

4. An obstetric vacuum extractor according to claim 3, in which the cup is less than a full hemi-sphere in shape, having a polar region away from its substantially circular rim.

5. An obstetric vacuum extractor according to claim 1, in which the skirt is circular in plan form and extends continuously around the inner surface of the cup.

6. An obstetric vacuum extractor according to claim 1, in which the inner surface of the cup has a central vacuum entry port and a series of channels spreading from said central vacuum entry port.

7. An obstetric vacuum extractor according to claim 1, in which the flexible integrally formed, hollow extension is rotatable relative to the cup both in a first plane parallel to a plane containing the rim of the cup and in a second plane at right angles to the first plane.

8. An obstetric vacuum extractor according to claim 7, in which the extension can flex through at least 180° in the first plane and at least 180° in the second plane while still enabling a vacuum to be applied.

9. An obstetric vacuum extractor according to claim 1, in which the flexible integrally formed hollow extension is a short extension to which is connected a longer hollow flexible extension shaft.

10. An obstetric vacuum extractor according to claim 1, which is an injection moulding of a silicone rubber or a polyurethane.

11. An obstetric vacuum extractor according to claim 1, in which the rim of the cup is thickened.

12. An obstetric vacuum extractor according to claim 1, in which a handle is mounted transversely on the hollow extension, the handle having a transverse passageway to align with a hollow passageway through the hollow extension to the interior of the cup.

13. An obstetric vacuum extractor according to claim 1, which is provided with means to ensure separation of the handle from the cup if a predetermined force is exceeded.

14. An obstetric vacuum extractor according to claim 13, wherein when the handle is attached to the hollow extension the handle gradually pulls out of the extension as the force used increases and exposes an indicator on the extension.

15. An obstetric vacuum extractor according to claim 1, in which the hollow extension is a hollow shaft extending generally tangentially to the cup and being joined to the cup by a curved end portion of the hollow shaft.

16. An obstetric vacuum extractor according to claim 1, in which the hollow extension is normal to the surface of the cup to which it is connected by a narrow neck portion.

17. An obstetric vacuum extractor according to claim 1, in which orientation guide means are moulded on the exterior surface of the cup.

18. An obstetric vacuum extractor according to claim 1, in which finger holds are moulded on the exterior surface of the cup.

19. An obstetric vacuum extractor according to claim 1, which is a compression moulding of silicone rubber or a polyurethane.

* * * * *